United States Patent [19]

Orvik

[11] 4,327,220

[45] Apr. 27, 1982

[54] PROCESS FOR REDUCING PICOLINE DERIVATIVES USING COPPER CATALYST

[75] Inventor: Jon A. Orvik, Danville, Calif.

[73] Assignee: The Dow Chemical Company, Midland, Mich.

[21] Appl. No.: 220,392

[22] Filed: Dec. 29, 1980

[51] Int. Cl.³ .................. C07D 213/26; C07D 213/64
[52] U.S. Cl. .................................... 546/345; 546/301; 546/302; 546/346
[58] Field of Search ................ 546/345, 346, 301, 302

[56] References Cited

U.S. PATENT DOCUMENTS

| | | | |
|---|---|---|---|
| 3,420,833 | 1/1969 | Taplin | 546/138 |
| 3,591,596 | 7/1971 | Wang et al. | 546/294 |
| 4,062,962 | 12/1977 | Noveroske | 424/263 |
| 4,143,144 | 3/1979 | Tobol et al. | 424/263 |
| 4,260,766 | 4/1981 | Morris | 546/303 |

*Primary Examiner*—Alan L. Rotman
*Attorney, Agent, or Firm*—S. Preston Jones; Robert R. Stringham; Ronald G. Brookens

[57] ABSTRACT

Reducing trichloromethyl substituent on pyridine ring to dichloromethyl using a copper catalyst and a reducing agent.

5 Claims, No Drawings

PROCESS FOR REDUCING PICOLINE DERIVATIVES USING COPPER CATALYST

BACKGROUND OF THE INVENTION

Various derivatives of phenoxypyridine, such as cyano-(6-phenoxy-2-pyridinyl)methyl-3-(2,2-dichloroethenyl)-2,2-dimethylcyclopropane carboxylate, are useful as pesticides. One method of preparing this class of compounds is through an intermediate which is a derivative of alpha-dichloromethylpyridine. This derivative is most conveniently prepared by reducing the corresponding trichloromethyl derivative. Reducing agents such as iron metal, zinc, or stannous and ferrous salts have been used to effect this reduction. Since these reducing agents generally must be present in stoichiometric amounts, these prior art processes have the disadvantage of requiring the disposal of large amounts of heavy metal wastes. The present invention is a process for carrying out the reduction without the generation of large quantities of heavy metal wastes.

SUMMARY OF THE INVENTION

This invention relates to a process for reducing a trichloromethyl substituent in the 2- position of a pyridine ring to a dichloromethyl group which comprises treating a compound of the formula

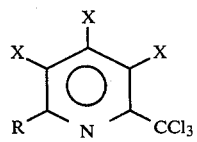

with stoichiometric amounts of water and an effective reducing agent in the presence of a catalytic amount of copper at a temperature of from about 40° C. to about 150° C. in the presence of a suitable solvent for a time sufficient to convert at least some of the tirchloromethyl substituent to dichloromethyl, wherein X independently and at each occurrence represents chlorine or hydrogen and R represents hydrogen, chlorine, phenoxy or substituted phenoxy. As used herein, the term substituted phenoxy refers to a phenoxy moiety containing one or more substituents which do not detrimentally affect the reduction of the trichloromethyl group. Such a substituted phenoxy moiety may contain one or more substituents such as, for example, lower alkyl, lower alkoxy, halo, etc.

Catalytic amount refers to that amount of the copper which is necessary to catalyze the reduction of the trichloromethyl substituent to dichloromethyl. This amount may vary somewhat depending upon the reaction conditions employed. Thus, such factors as tempratture, starting material, and solubility in the solvent may affect the precise amount of catalyst required to carry out the reduction. Solvents suitable for use in the process of this invention include polar solvents in which the pyridine compound is soluble, such as lower alcohols, ketones and aliphatic carboxylic acids. Thus suitable solvents include methanol, ethanol, propanol, butanol, acetone, methylethylketone, methylisobutylketone, acetic acid, propionic acid, and butyric acid.

DETAILED DESCRIPTION OF THE INVENTION

In carrying out the process that is the subject of this invention, a stoichiometric amount of an effective reducing agent must be present. The reducing agent may be any reducing agent, other than those containing a heavy metal, which is capable of reducing the trichloromethyl group in the presence of the copper. Preferred reductants are phosphorous acid and hypophosphorous acid. Effective reducing agents also include potassium or sodium bisulfite. Other reducing agents which are believed to be effective include sulfur dioxide, ascorbic acid, hydroquinone, as well as certain anions such as, for example, dithionite ion, thiosulfate ion, and iodide ion.

It is sometimes desirable to add a small amount, e.g., about 5 mole % has been found satisfactory, of aqueous hydrochloric acid to the reaction initially to aid in solubilizing the copper. Hydrogen chloride is produced as a product during the reaction, so only enough to insure the presence of some soluble copper during the initial stage of the reaction is necessary.

The reduction reaction using hypophosphorous acid may be summarized for 6-chloro-2-dichloromethylpyridine as follows:

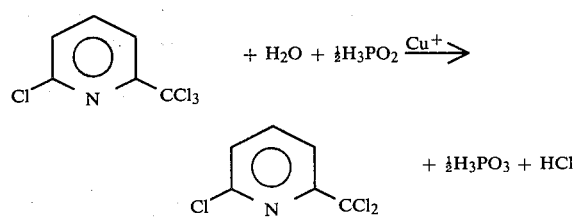

The same reduction using sulfur dioxide may be represented as follows:

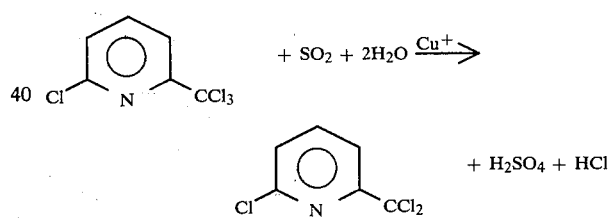

The reduction will proceed at temperatures of from about 40° C. to about 150° C., with a temperature of from about 70° C. to about 110° C. being preferred. The reduction will occur readily over a wide range of pressures; however, atmospheric pressure is generally preferred for convenience.

One reactive form of copper is known to be the monovalent (cuprous) form; however, those skilled in the art will recognize that copper may be added in its various other forms to the reaction mixture and converted to the monovalent form therein. Thus, divalent copper or even copper metal may be added to the reaction mixture and converted to monovalent copper. From a practical viewpoint, this may be preferable, since the monovalent form is generally less stable than the divalent and metallic forms. There is also some evidence metallic copper may be able to serve as a catalyst in the reduction without being converted to the monovalent form.

The term catalyst as used herein is applied in its broadest sense, i.e., a substance which when present in a small quantity will produce an effect in a chemical reaction and may be recovered unchanged at the completion of the reaction.

The following example will serve to further illustrate the invention, but should not be construed as a limitation thereon.

EXAMPLE 1

The starting material, 6-chloro-2-trichloromethylpyridine, (11.6 grams; 0.05 mole) was dissolved in 25 ml of warm glacial acetic acid and placed in a reaction vessel. Cupric oxide (0.5 gm; 0.0062 mole) and concentrated hydrochloric acid (6 ml) were added with stirring. The temperature of the reaction mixture was raised to 70°–75° C. Hypophosphorous acid (3.3 grams of 50% acid; 0.025 mole) was gradually added to the stirred mixture. The temperature of the mixture increased as a result of exotherm during the addition period. The temperature was maintained at about 90° C. for one hour. After one hour the acetic acid was distilled under vacuum and the residue was taken up in 25 ml of toluene and 25 ml of water. The toluene was washed three times with water and dried over sodium sulfate. Upon evaporation of the toluene, 8.6 grams of a light colored oil remained which crystallized into an off-white solid which was identified by external standard gas chromatography as containing 95% of the reduced starting material, i.e., 6-chloro-2-dichloromethylpyridine.

EXAMPLE 2

A 100 gal. Pfauder kettle was charged with 11 pounds of cupric chloride dihydrate dissolved in 2 gal. of water. To this mixture was added 225 pounds of acetic acid, 270 pounds of 2-chloro-6-trichloromethyl pyridine (93.9% pure) and 225 pounds of additional acetic acid. The mixture was agitated, and the temperature of the reaction mixture raised to 80° C. Over a period of two hours and forty-five minutes 27 liters of 50% hypophosphorous acid was added, followed by four to five hours of heating (80°–85° C.). The acetic was stripped under vacuum, and the contents were cooled to 60° C. Toluene (55 gal.) and water (24 gal.) were added and the mixture allowed to settle. The organic layer was separated and the product recovered as a solution. Analysis of the toluene solution using external standard glc method showed 84% of 6-chloro-2-dichloromethylpyridine. An additional 12% of product was identified in the interfacial emulsion and acetic acid overhead. Therefore, total yield was found to be 96%.

What is claimed is:

1. A process for reducing a trichloromethyl group in the 2-position of a pyridine ring to a dichloromethyl group which comprises treating a compound corresponding to the formula

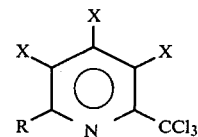

wherein each X independently represents hydrogen or chloro and R represents hydrogen, chloro, phenoxy or phenoxy substituted with one or more lower alkyl, lower alkoxy or halo groups with a stoichiometric amount of water and a catalyst which is a monovalent or divalent copper compound or metallic copper in an amount which is sufficient to catalyze said reduction and a reducing agent capable of said reduction in the presence of said copper catalyst, said treating being carried out at a temperature of from about 40° C. to about 150° C. and in the presence of a solvent for a time sufficient to convert the trichloromethyl group to a dichloromethyl group.

2. The process of claim 1 wherein the copper catalyst is a monovalent copper compound and the reducing agent is selected from the group consisting of phosphorous acid, hypophosphorous acid, potassium bisulfite, sodium bisulfite, sulfur dioxide, ascorbic acid, hydroquinone, dithionite ion, thiosulfate ion, and iodide ion.

3. The process of claim 2 wherein the reducing agent is phosphorous acid or hypophosphorous acid.

4. The process of claims 1, 2 or 3 wherein the reduction is carried out at a temperature of from about 70° C. to about 110° C.

5. The process of claim 1 wherein the starting material is 6-chloro-2-trichloromethylpyridine.

* * * * *